United States Patent
Osterloh (10) Patent No.: US 7,311,338 B2
(45) Date of Patent: Dec. 25, 2007

(54) REMOTELY OPERATED EQUIPMENT COUPLER

(75) Inventor: James Osterloh, West Richland, WA (US)

(73) Assignee: Parsons Corporation, Pasadena, CA (US)

( * ) Notice: Subject to any disclaimer, the term of this patent is extended or adjusted under 35 U.S.C. 154(b) by 465 days.

(21) Appl. No.: 10/948,499

(22) Filed: Sep. 22, 2004

(65) Prior Publication Data

US 2006/0061091 A1     Mar. 23, 2006

(51) Int. Cl.
F16M 1/00 (2006.01)
F16L 39/00 (2006.01)
H01R 4/60 (2006.01)
H01R 13/62 (2006.01)

(52) U.S. Cl. ............... 285/124.1; 285/24; 248/648; 248/651; 248/657; 248/671; 248/672; 439/191; 439/310

(58) Field of Classification Search ............ 248/637, 248/639, 648, 651, 657, 671, 672; 285/24–26, 285/124.1, 124.2, 124.3, 124.4, 124.5; 439/191, 439/310
See application file for complete search history.

(56) References Cited

U.S. PATENT DOCUMENTS

| | | | |
|---|---|---|---|
| 4,507,707 A * | 3/1985 | Willis | 361/679 |
| 5,342,098 A * | 8/1994 | Wilkins | 285/26 |
| 5,582,523 A * | 12/1996 | Noro et al. | 439/310 |
| 5,884,664 A * | 3/1999 | Nagai et al. | 137/884 |
| 6,017,065 A * | 1/2000 | Helles.o slashed.e | 285/25 |
| 6,783,380 B1 * | 8/2004 | Kamath et al. | 439/247 |
| 7,146,999 B2 * | 12/2006 | Giese et al. | 137/269 |
| 2004/0070200 A1 * | 4/2004 | Campbell et al. | 285/124.1 |
| 2005/0184510 A1 * | 8/2005 | Langenfeld et al. | 285/124.1 |

\* cited by examiner

Primary Examiner—James M. Hewitt
(74) Attorney, Agent, or Firm—Denton L. Anderson; Sheldon Mak Rose & Anderson PC (57) ABSTRACT

A modular chemical handling apparatus has a first component coupled to a second component. The first component is retained proximate to the second component by a locking mechanism. Fluid conduit connection devices and/or electrical connection devices in the first component are coupled to corresponding conduit connection devices and/or electrical connection devices in the second component by couplers. At least one laterally sliding lock shaft is employed for coupling the first module to the second module and for decoupling the first module from the second module. In one embodiment, counterweights are used to maintain the sliding lock shaft and each of the connection devices in the fully coupled position.

15 Claims, 12 Drawing Sheets

REMOTELY OPERATED EQUIPMENT COUPLER

FIELD OF THE INVENTION

This invention relates generally to equipment couplers and, more specifically, to equipment couplers used in hazardous operating environments.

BACKGROUND OF THE INVENTION

A large number of chemical handling operations have to be conducted in sealed areas because the chemicals being handled are highly toxic. This group of operations includes processes for handling radioactive materials.

Maintenance on the chemical handling equipment used in such operations is extremely awkward, because it has to be performed in the ultra-hazardous sealed area. The maintenance could be greatly simplified, however, if the chemical handling equipment could be modular in construction, and could be decoupled and recoupled by remote means. The ability to decouple individual modules of the chemical handling equipment would allow the transport of such modules in need of maintenance to a decontamination area where the module could be detoxified. After being detoxified, maintenance on the module could be accomplished safely and in an ordinary work area. The module could then be recoupled to the remainder of the chemical handling equipment, again, preferably, by remotely controlled means.

To accomplish this, there is a need for a remotely controlled equipment coupler capable of being used with chemical handling equipment.

SUMMARY

The invention satisfies this need. The invention is a modular apparatus which has at least one fluid stream conduit or one electrical circuit. The apparatus comprises (a) a first apparatus component attached to a cradle, the cradle having at least one cradle support strut, the at least one cradle support strut comprising a first locking moiety, the first apparatus component also having at least one conduit connection or one electrical connection moiety; (b) a second apparatus component having at least one conduit connection or electrical connection moiety, each of the at least one conduit connection or electrical connection moieties of the second apparatus component being operatively aligned with one of the at least one conduit connection or electrical connection moieties of the first apparatus component to form one or more corresponding pairs of conduit connection or electrical connection moieties, each corresponding pair of conduit connection or electrical connection moieties being (i) connectable to one another by axial thrusting of one moiety of the corresponding pair of conduit connection or electrical connection moieties towards the other moiety, and (ii) disconnectable by axial withdrawal of one moiety in the corresponding pair of conduit connection or electrical connection moieties away from the other moiety in that corresponding pair of conduit connection or electrical connection moieties; (c) at least one sliding lock shaft attached to the second apparatus component, the at least one sliding lock shaft having a cradle seat for accepting and retaining the at least one cradle support strut, the cradle seat comprising a second locking moiety capable of engaging the first locking moiety to firmly secure the at least one cradle support strut to the cradle seat, the at least one sliding lock shaft being laterally moveable between (i) a first sliding lock shaft position wherein the second locking moiety is engaged with the first locking moiety so as to firmly secure the at least one cradle support strut to the cradle seat, and (ii) a second sliding lock shaft position wherein the second locking moiety is disengaged from the first locking moiety so that the at least one support strut is capable of being lifted off of the cradle seat; (d) coupling means for urging the sliding lock shaft to the first sliding lock shaft position and for urging each conduit connection and electrical connection moiety in the second apparatus component towards a corresponding conduit connection or electrical connection moiety in the first apparatus component in such a way that each conduit connection and electrical connection moiety in the second apparatus component is operatively coupled to a corresponding conduit connection or electrical connection moiety in the first apparatus component; and (e) decoupling means for urging the sliding lock shaft to the second sliding lock shaft position and for urging each conduit connection and electrical connection moiety in the second apparatus component away from a corresponding conduit connection or electrical connection moiety in the first apparatus component in such a way that each conduit connection and electrical connection moiety in the second apparatus component is effectively decoupled from all conduit connection and electrical connection moieties in the first apparatus component, whereby the second apparatus component can be physically separated from the first apparatus component.

In a typical embodiment, the coupling means is provided by one or more counterweights which act through rack and pinion gears to exert sufficient continuous lateral pressure on the corresponding pairs of connection moieties and on the sliding lock shafts to maintain the first apparatus component firmly coupled to the second apparatus component.

DRAWINGS

These features, aspects and advantages of the present invention will become better understood with regard to the following description, appended claims and accompanying figures where:

DETAILED DESCRIPTION

The following discussion describes in detail one embodiment of the invention and several variations of that embodiment. This discussion should not be construed, however, as limiting the invention to those particular embodiments. Practitioners skilled in the art will recognize numerous other embodiments as well.

The invention is a modular apparatus 10 typically useable in the handling of one or more chemical flow streams. The apparatus 10 has at least one fluid stream conduit 12 or at least one electrical conductor 14. The apparatus 10 is constructed in modular form and has a first apparatus component 16 which is coupled to a second apparatus component 18. The first apparatus component 16 is decouplable and recouplable to the second apparatus component 18 by remotely controlled means.

Figure 1:
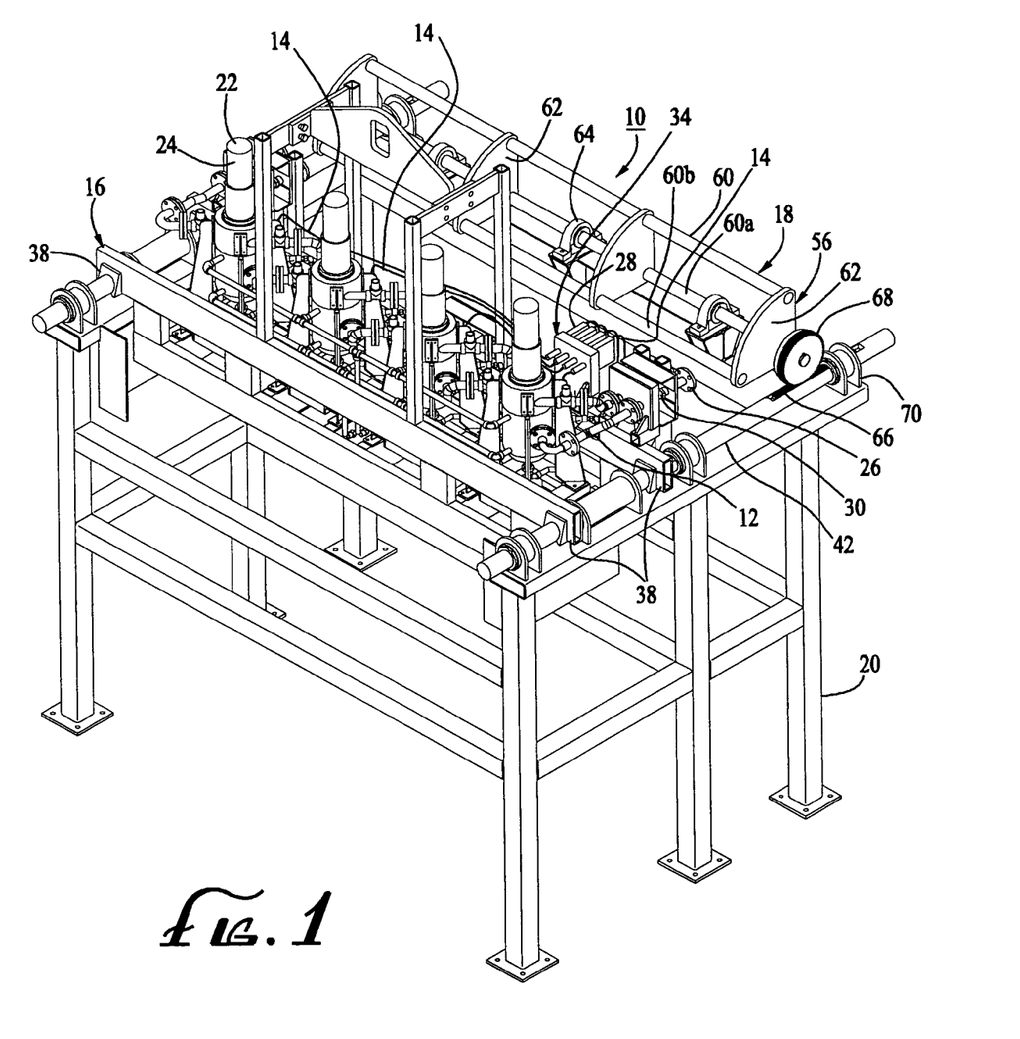
FIG. 1 is a perspective view of a modular apparatus having features of the invention.
Figure 2:
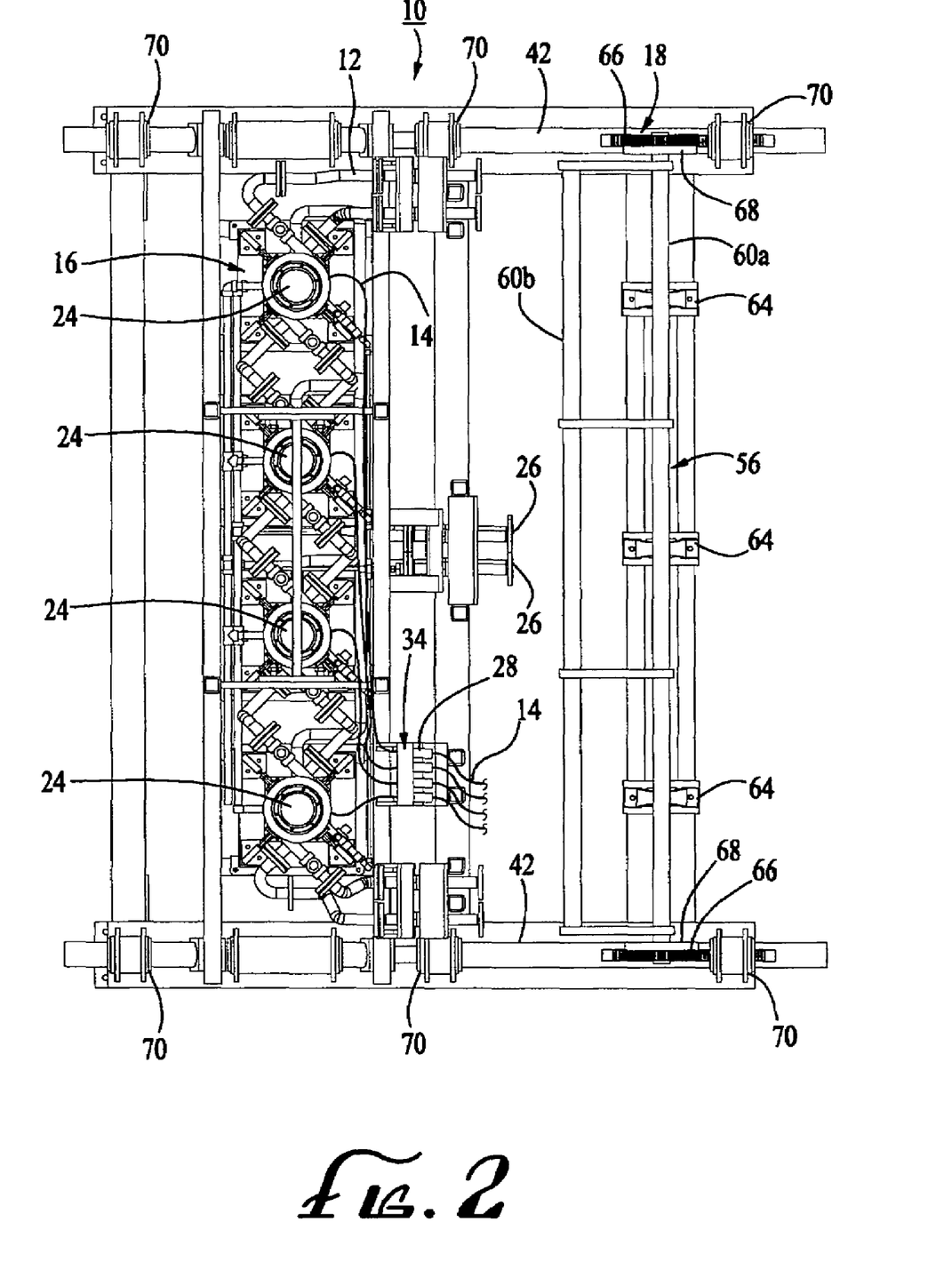
FIG. 2 is a plan view of the apparatus illustrated in FIG. 1.
Figure 3:
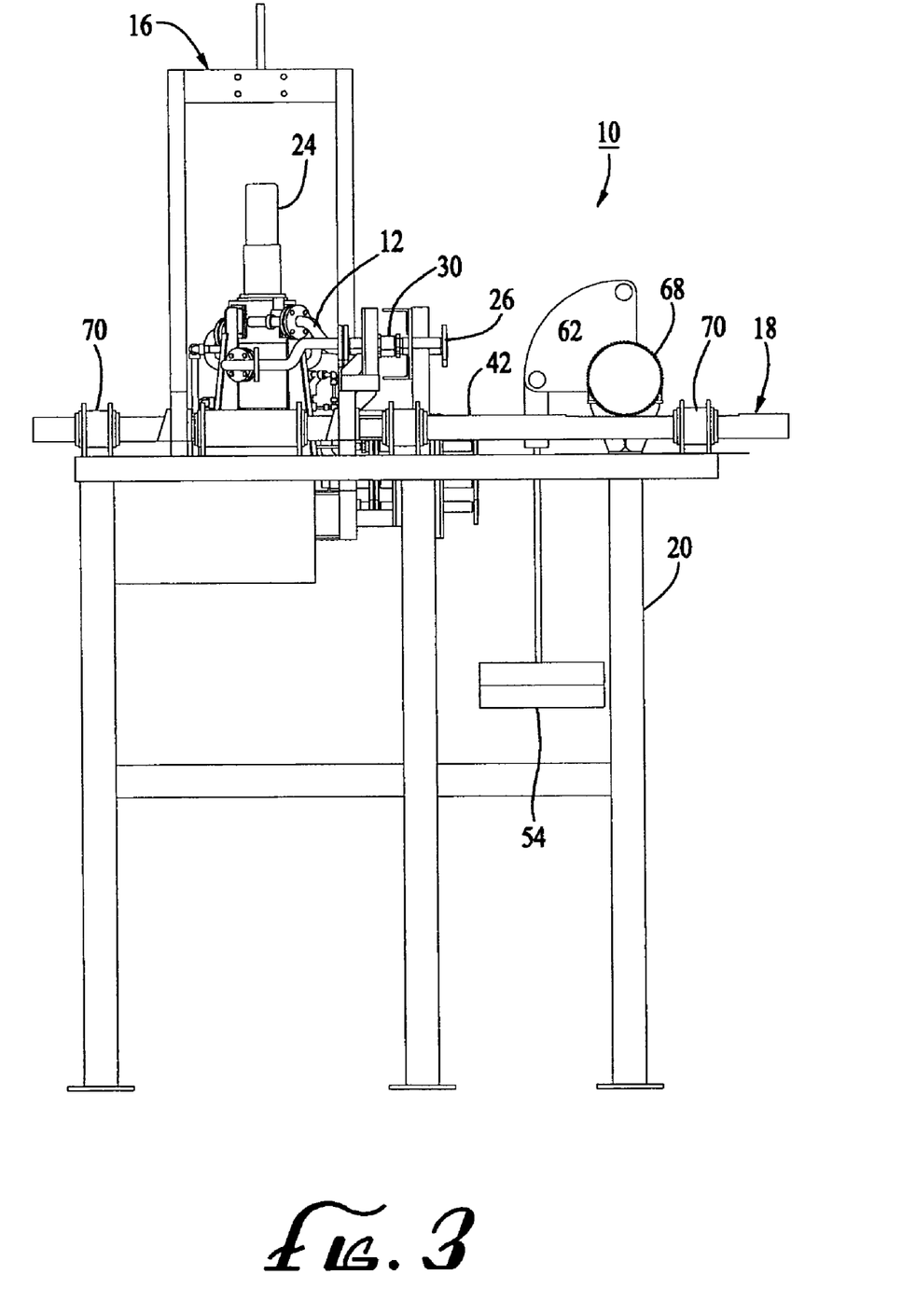
FIG. 3 is a side view of the of the apparatus illustrated in FIG. 1.

A typical modular apparatus 10 of the invention is illustrated in FIGS. 1-3. In the embodiment illustrated in the drawings, the first apparatus component 16 comprises a plurality of chemical handling devices 22, including four separation columns 24. Instead of, or in addition to, the four separation columns 24, the first apparatus component 16 could comprise other types of chemical processing and/or chemical handling devices 22, such as one or more pumps, heaters, reactors, separators, etc.

Figures 4, 5:
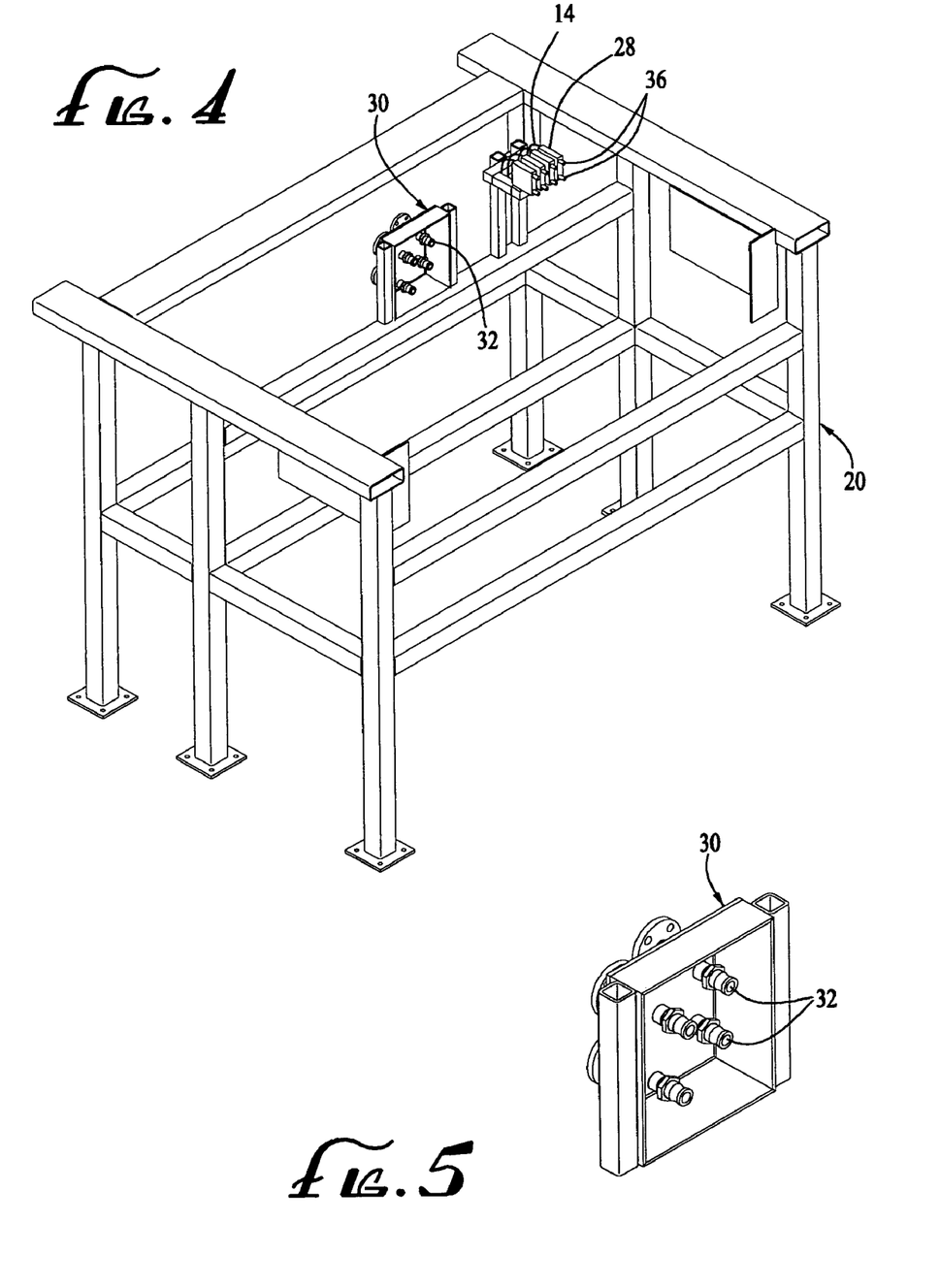
FIG. 4 is a perspective view of a framework used with the apparatus illustrated in FIG. 1.
FIG. 5 is a detail view of fluid conduit coupling components useful in the invention.

Typically, the second apparatus component 18 provides a support structure for the first apparatus component 16. The second apparatus component includes a framework 20, as illustrated in FIG. 4.

Where the apparatus 10 has one or more fluid stream conduits 12, and where those fluid stream conduits 12 run between the first apparatus component 16 and the second apparatus component 18, each fluid stream conduit 12 is coupled at the juncture of the first apparatus component 16 and the second apparatus component 18 by a fluid stream conduit coupler 30, comprising a corresponding pair of cooperating conduit connection moieties 32. Such a fluid stream conduit coupler 30 is illustrated in FIG. 5. This type of fluid stream conduit coupler 30 is well-known in the art.

Similarly, where the apparatus 10 has one or more electrical conductors 14 which run between the first apparatus component 16 and the second apparatus component 18, each electrical conductor 14 is coupled at the juncture of the first apparatus component 16 and the second apparatus component 18 by an electrical conductor coupler 34, comprising a corresponding pair of cooperating electrical connection moieties 36. Such an electrical conductor coupler 34 is illustrated in detail in FIG. 6. This type of electrical conductor coupler 34 is well-known in the art. Like the fluid stream conduit couplers 30, each electrical conductor coupler 34 consists of a corresponding pair of cooperating electrical connection moieties 36.

Figures 6, 9, 10:
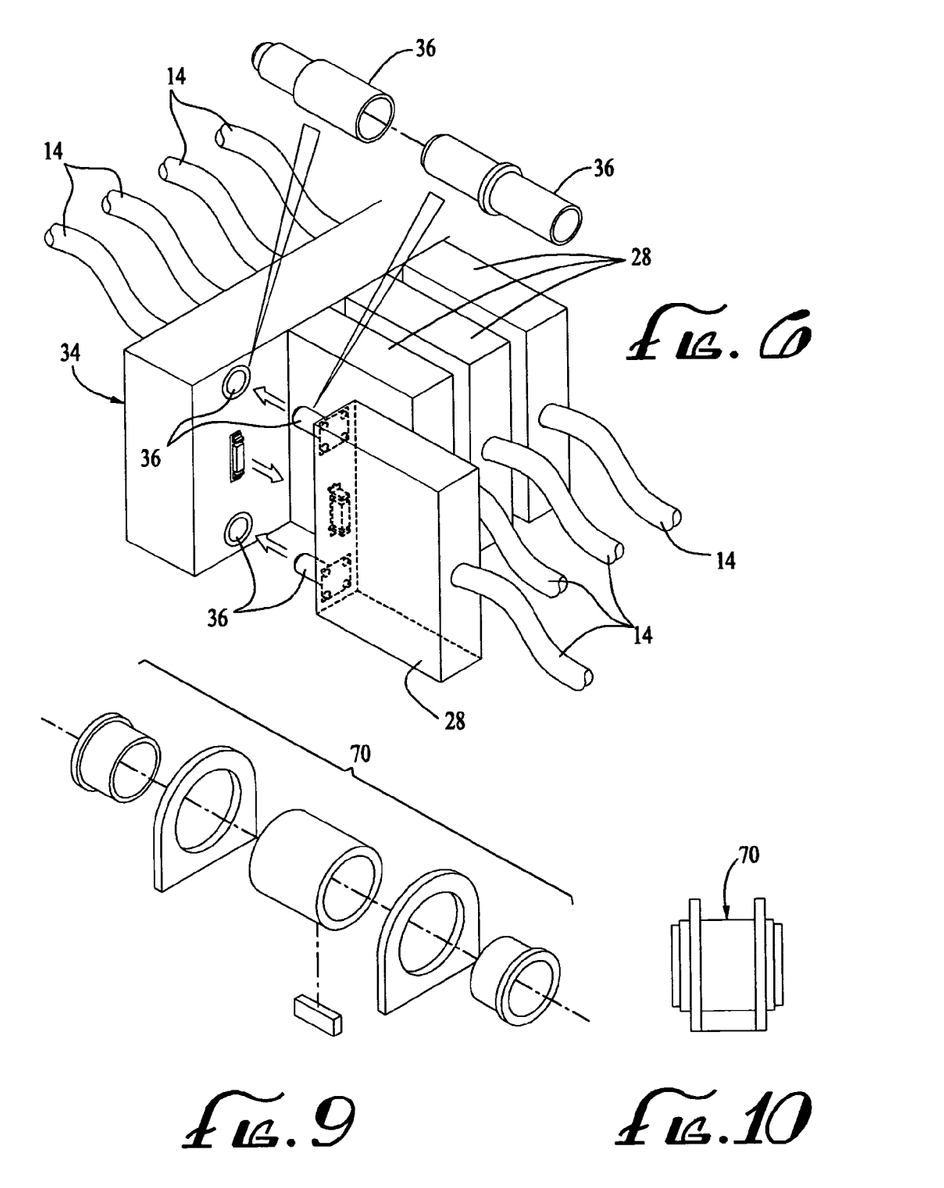
FIG. 6 is an exploded detail view of electrical coupling components useful in the invention.
FIG. 9 is an exploded view of a bearing useful in the invention.
FIG. 10 is a side view of the bearing illustrated in FIG. 9.
Figure 7:
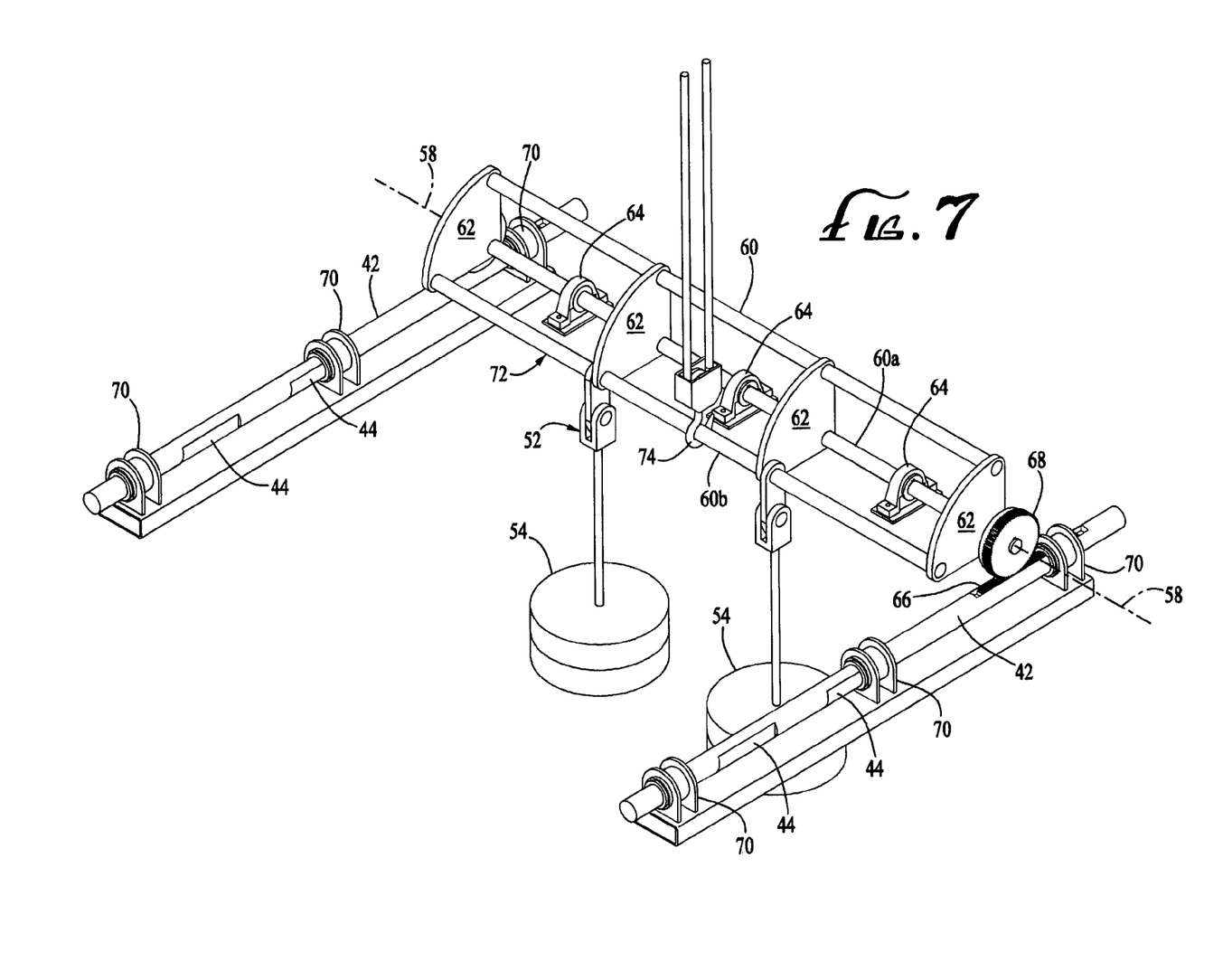
FIG. 7 is a perspective view of specific components of the apparatus illustrated in FIG. 1, the specific components being useful in the remote coupling and decoupling of sections of the apparatus.
Figure 8:
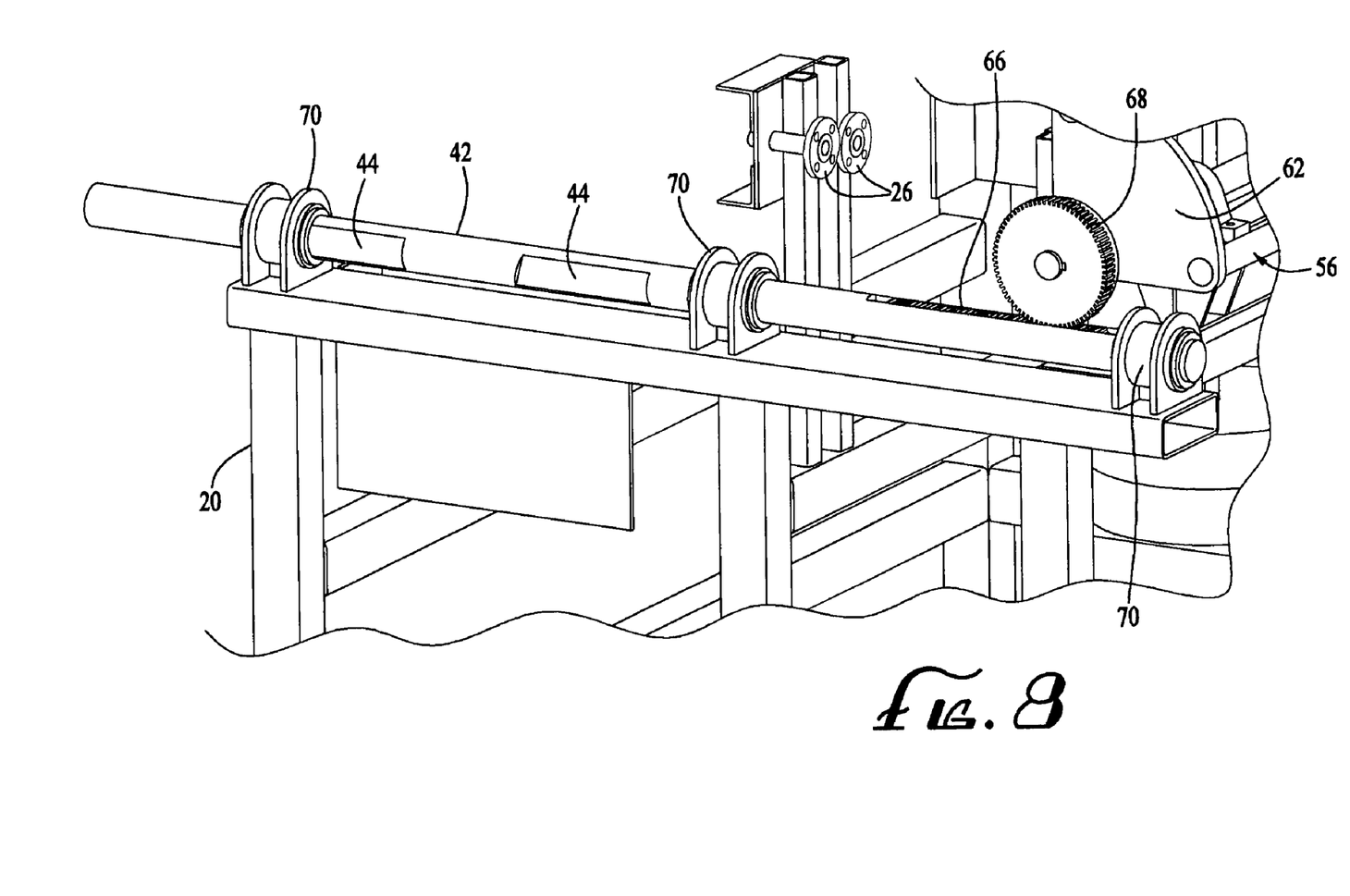
FIG. 8 is another perspective view showing the specific components of the apparatus illustrated in FIG. 7.

Each corresponding pair of fluid conduit connection moieties 32 or electrical connection moieties 36 are (i) connectable to one another by axial thrusting of one moiety in the corresponding pair of fluid conduit connection moieties 32 or electrical connection moieties 36 towards the other moiety, and (ii) disconnectable by axial withdrawal of one moiety in the corresponding pair of conduit connection moieties 32 or electrical connection moieties 36 away from the other moiety in that corresponding pair of fluid connection conduit moieties 32 or electrical connection moieties 36.

The first apparatus component 16 further comprises at least one cradle support strut 38 having a first locking moiety 40. In the embodiment illustrated in the drawings, the first apparatus component 16 has two cradle support struts 38, each disposed at a lower corner of the first apparatus component 16. At least one, and preferably both of the cradle support struts 38 comprise a first locking moiety 40.

The apparatus 10 also comprises at least one sliding lock shaft 42 attached to the second apparatus component 18. In the embodiment illustrated in the drawings, the apparatus 10 comprises a pair of sliding lock shafts 42, disposed in parallel. The sliding lock shafts 42 and related appurtenances are illustrated in detail in FIGS. 7, 8, 11 and 12. Each sliding lock shaft 42 has one or more cradle seats 44 for accepting and retaining a cradle support strut 38. In the embodiment illustrated in the drawings, each sliding lock shaft 42 comprises a pair of spaced apart cradle seats 44. Each cradle seat 44 comprises a second locking moiety 46 capable of engaging a first locking moiety 40 at the end of a cradle support structure 38, in such a way that the cradle support strut 38 is firmly secured to the cradle seat 44.

Each sliding lock shaft 42 is laterally moveable between (i) a first sliding lock shaft position wherein the second locking moiety 46 is engaged with the first locking moiety 40 so as to firmly secure at least one cradle support strut 38 to a cradle seat 44, and (ii) a second sliding lock shaft position wherein the second locking moiety 46 is disengaged from the first locking moiety 40, so that the support strut 38 is capable of being lifted off of the cradle seat 44.

Figure 11:
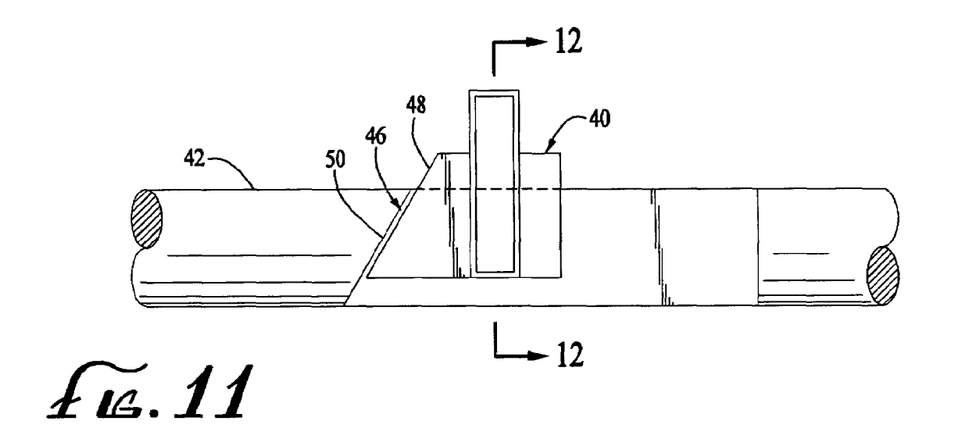
FIG. 11 is a detailed side view of a locking mechanism useful in the invention.
Figure 12:
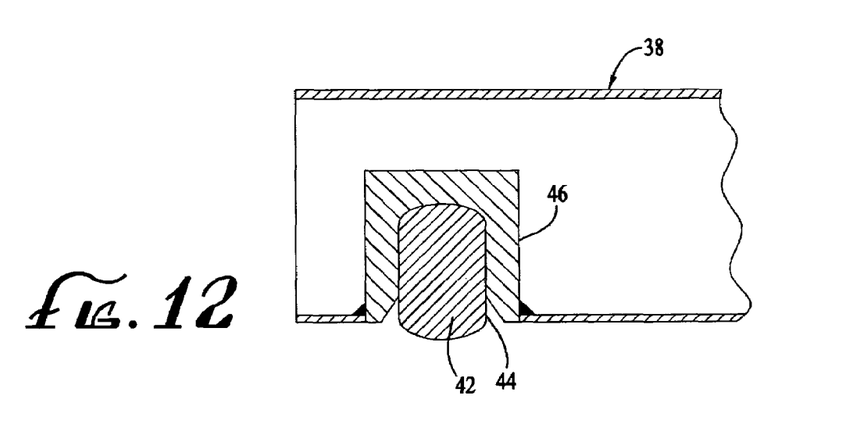
FIG. 12 is a cross-sectional view of the locking mechanism illustrated in FIG. 11, taken along line 12-12.

The first locking moiety 40 and the second locking moiety 46 are illustrated in detail in FIGS. 11 and 12. As can be seen in these figures, the first locking moiety 40 can comprise a beveled shoulder 48 and the second locking moiety 46 can comprise a corresponding chamfer 50 disposed at substantially the same angle as the beveled shoulder 48. When the sliding lock shaft 42 is in the first sliding lock shaft position, the beveled shoulder 48 cooperates with the chamfer 50 to firmly secure the cradle support strut 38 to the cradle seat 44, thus preventing the vertical removal of the cradle support strut 38 from the cradle seat 44. Those of skill in the art will recognize that a wide variety of alternative locking moiety configurations can also be used in the invention.

The apparatus 10 further comprises coupling means 52 for urging the sliding lock shafts 42 to the first sliding lock shaft position and for urging each fluid conduit connection moiety 32 and each electrical connection moiety 36 in the second apparatus component 18 towards a corresponding fluid conduit connection moiety 32 or electrical connection moiety 36 in the first apparatus component 16 in such a way that each fluid conduit connection 32 and electrical connection moiety 36 in the second apparatus component 18 is operatively coupled to a corresponding fluid conduit connection 32 or electrical connection moiety 36 in the first apparatus component 16. Such coupling means 52 can be provided by a wide variety of mechanical, electrical, hydraulic and pneumatic equipment.

In the embodiment illustrated in the drawings, a preferred coupling means 52 comprises one or more counterweights 54. The counterweights 54 depend from an elongate rotatable structure 56 capable of rotating around a rotation axis 58. The counterweights 54 are suspended from a portion of the elongate rotatable structure 56 which is spaced apart from the rotation axis 58, so that the lowering of the counterweights 54 rotates the elongate rotatable structure 56 about the rotation axis 58. In the embodiment illustrated in the drawings, the elongate rotatable structure 56 comprises three parallel rods 60 held together in fixed orientation with respect to one another by four spacers 62. A first rod 60*a* is journaled within three bearings 64 and is rotatable within those bearings 64. The counterweights 54 are suspended from a second rod 60*b* spaced apart from the first rod 60*a*. As can be seen, the raising of the second rod 60*b* necessarily causes the rotation of the elongate rotatable structure 56 in a direction opposite to the rotation of the elongate rotatable structure 56 caused by the lowering of the counterweights 54.

The elongate rotatable structure 56 is operatively connected to the sliding lock shafts 42 by racks 66 and pinion gears 68 in such a way that the rotation of the pinion gears 68 within the racks 66 translates the rotational movement of the elongate rotatable structure 56 to lateral movement of the sliding lock shafts 42. The sliding lock shafts 42 are disposed within sliding lock shaft bearings 70 as illustrated in detail in FIGS. 9 and 10.

The use of the counterweights 54, operating through the racks 66 and pinion gears 68, are preferred in many applications because they exert a specific and constant coupling force which is not subject to failure from most of the mechanical, electrical, hydraulic and/or pneumatic breakdowns which other coupling means are subject to.

The apparatus 10 further comprises decoupling means 72 for urging the sliding lock shafts 42 to the second sliding lock shaft position and for urging each fluid conduit connection moiety 32 and electrical connection moiety 36 in the second apparatus 18 away from a corresponding fluid conduit connection moiety 32 or electrical connection moiety 36 in the first component 16, in such a way that each fluid conduit connection moiety 32 and electrical connection moiety 36 in the second apparatus component 18 is effectively decoupled from all fluid conduit connection moieties 32 and electrical connection moieties 36 in the first apparatus component 16. Such decoupling means 72 can be provided by a wide variety of mechanical, electrical, hydraulic and pneumatic devices known in the art.

In the embodiment illustrated in the drawings, the decoupling means 72 is merely provided by the second rod 60*b* on the elongate rotatable structure 56. By attaching a crane hook 74 on this second rod 60*b* and raising the crane hook 74, the elongate rotatable structure 56 is rotated in such a way that the sliding lock shafts 42 are moved to the second locking shaft position.

After the sliding lock shafts 42 are moved to the second sliding lock shaft position, each of the locking moieties 40 and 46 is disengaged, as are each of the fluid conduit connection moieties 32 and electrical connection moieties 36. Thus, the second apparatus component 18 can be physically separated from the first apparatus component 16.

Figure 13:
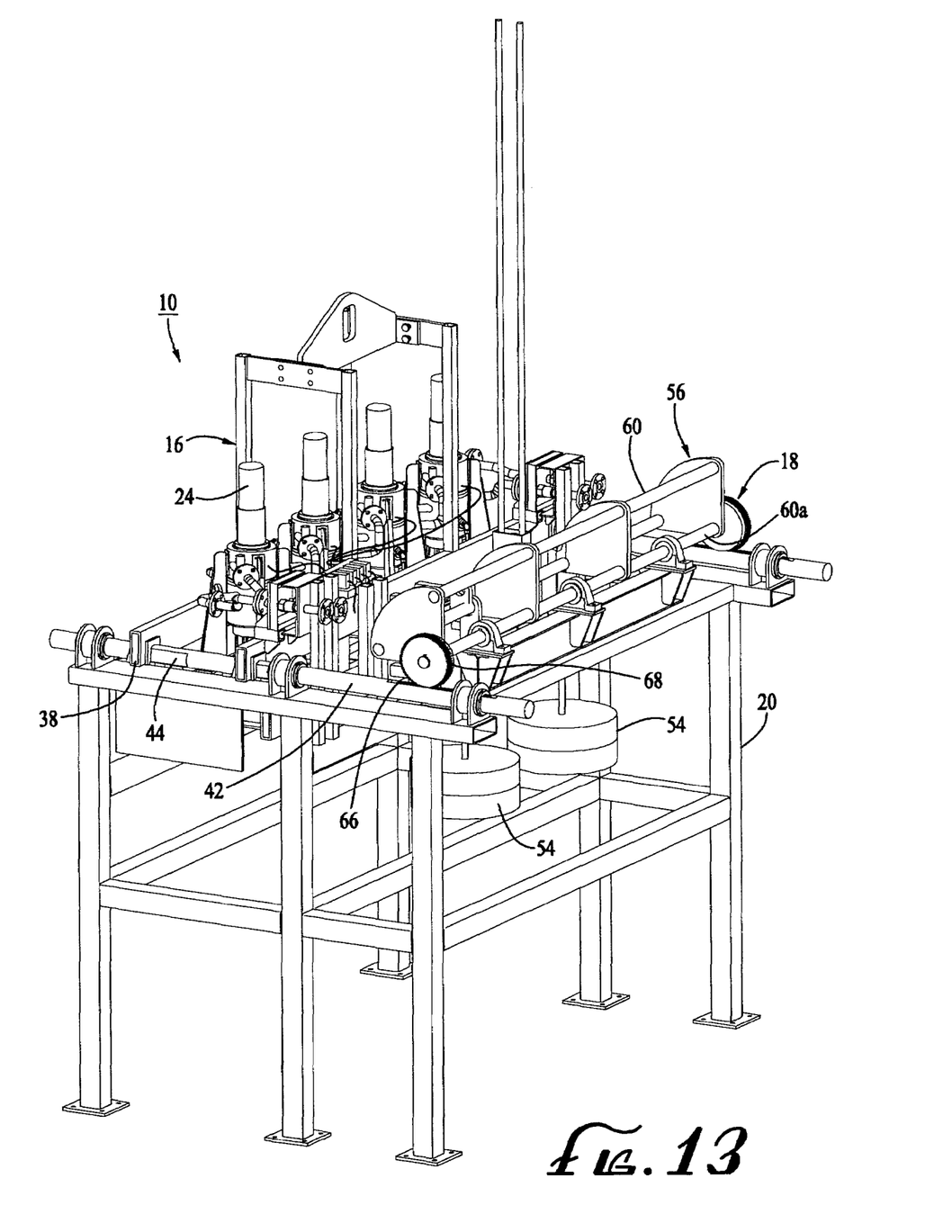
FIG. 13 is a second perspective view of the apparatus illustrated in FIG. 1, showing the initial stages of a decoupling operation.
Figure 14:
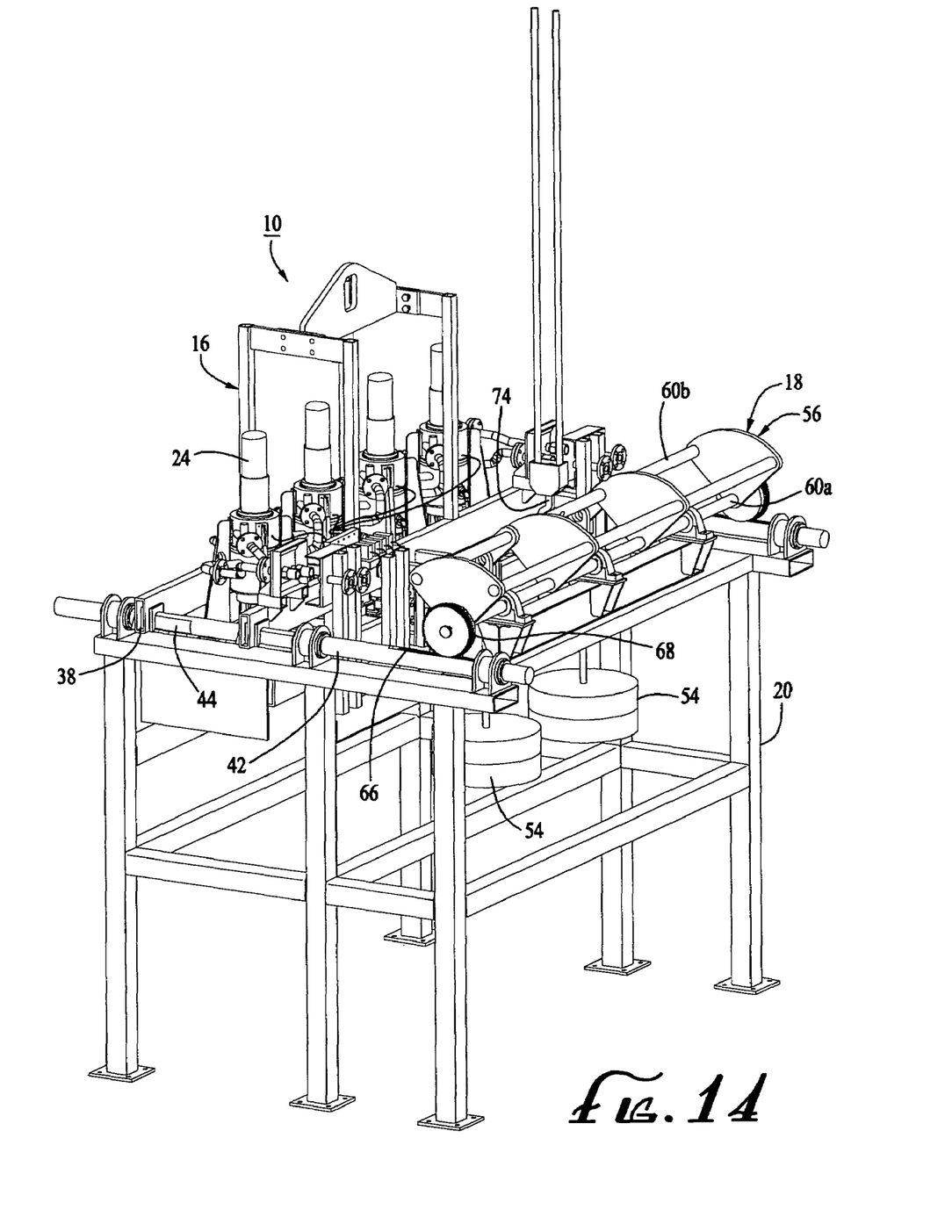
FIG. 14 is a second perspective view of the modular apparatus illustrated in FIG. 13, showing the decoupling operation in a more advanced stage.
Figure 15:
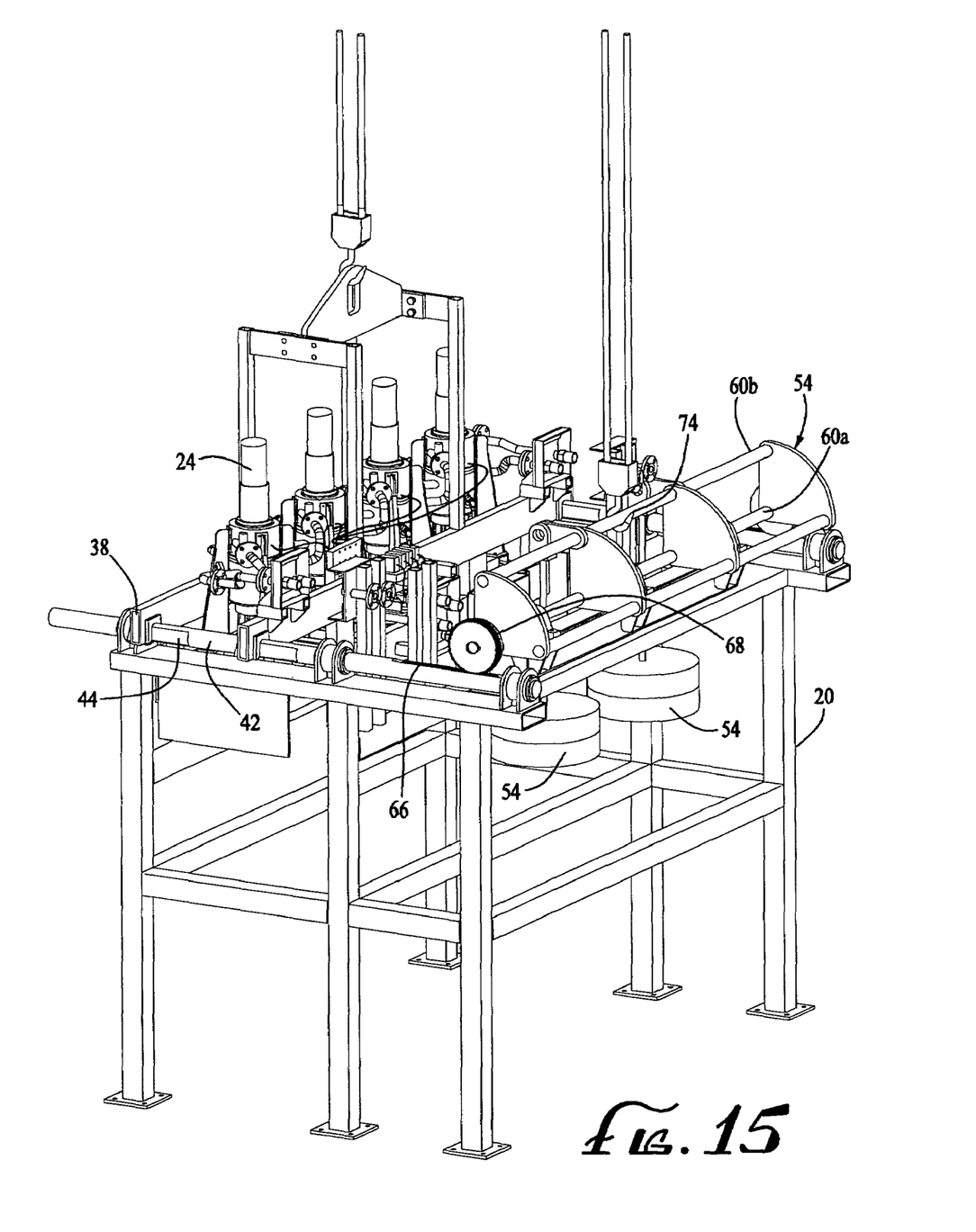
FIG. 15 is a third perspective view of the modular apparatus illustrated in FIG. 13, showing the decoupling operation in a still more advanced stage.
Figure 16:
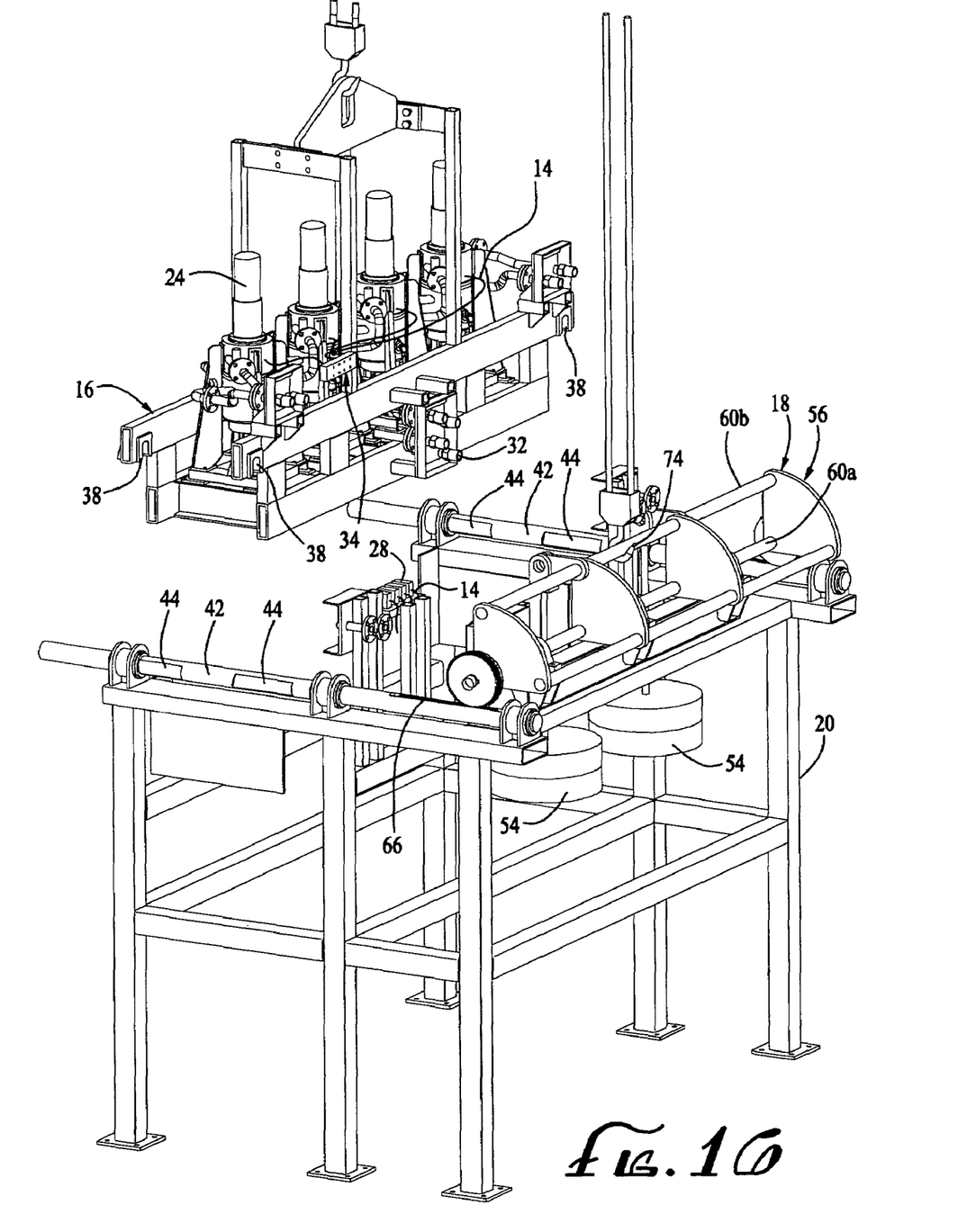
FIG. 16 is a fourth perspective view of the modular apparatus illustrated in FIG. 13, showing the decoupling operation in a final stage.

The decoupling of the first apparatus component 16 from the second apparatus component 18 is illustrated in FIGS. 13-16. FIG. 13 illustrates the first apparatus component 16 firmly coupled to the second apparatus component 18. Each of the sliding lock shafts 42 is in the first sliding lock shaft position. The hook 74 of a crane (not shown) has been lowered to a position proximate to the elongate rotatable structure 56. FIG. 14 illustrates how the crane hook 74 has been attached to the second rod 60*b* in the elongate rotatable structure 56 and has rotated the elongate rotatable structure 56 by raising the second rod 60*b*. As the elongate rotatable structure 56 is rotated, the pinion gears 68 act upon the racks 66 to slide the sliding lock shafts 42 from the first sliding lock shaft position towards the second sliding lock shaft position. FIG. 15 illustrates the two apparatus components 16 and 18 in a fully decoupled state. The crane has lifted the second rod 60*b* of the elongate rotatable structure 56 to its highest point. This has caused the racks 66 and pinion gears 68 to slide the sliding lock shafts 42 to the second sliding lock shaft position. Each of the fluid conduit connection moieties 32 and electrical connection moieties 36 at the junction between the first apparatus component 16 and the second apparatus component 18 have been separated from each other, and each of the locking moieties 40 and 46 is disengaged from its counterpart. FIG. 16 illustrates how a second crane (also not shown) can then be used to lift the first apparatus component 16 away from the second apparatus component 18 while the sliding lock shafts 42 are held in the decoupled position.

The recoupling of the first apparatus component 16 to the second apparatus component 18 can be simply accomplished by reversing the steps illustrated in FIGS. 13-16.

By operating the cranes remotely, the entirety of the decoupling and subsequent recoupling operations can be carried out without workers having to enter the ultrahazardous sealed area wherein the apparatus 10 is operated. The invention thus provides a major advancement in the safe and efficient operation of equipment carried out in hazardous operating environments.

Having thus described the invention, it should be apparent that numerous structural modifications and adaptations may be resorted to without departing from the scope and fair meaning of the instant invention as set forth hereinabove and as described hereinbelow by the claims.

What is claimed is:

1. A modular apparatus having at least one fluid stream conduit or one electrical circuit, the apparatus comprising:
    (a) a first apparatus component attached to a cradle, the cradle having at least one cradle support strut, the at least one cradle support strut comprising a first locking moiety, the first apparatus component also having at least one conduit connection or one electrical connection moiety;
    (b) a second apparatus component having at least one conduit connection or electrical connection moiety, each of the at least one conduit connection or electrical connection moieties of the second apparatus component being operatively aligned with one of the at least one conduit connection or electrical connection moieties of the first apparatus component to form one or more corresponding pairs of conduit connection or electrical connection moieties, each corresponding pair of conduit connection or electrical connection moieties being (i) connectable to one another by axial thrusting of one moiety of the corresponding pair of conduit connection or electrical connection moieties towards the other moiety, and (ii) disconnectable by axial withdrawal of one moiety in the corresponding pair of conduit connection or electrical connection moieties away from the other moiety in that corresponding pair of conduit connection or electrical connection moieties;
    (c) at least one sliding lock shaft attached to the second apparatus component, the at least one sliding lock shaft having a cradle seat for accepting and retaining the at least one cradle support strut, the cradle seat comprising a second locking moiety capable of engaging the first locking moiety to firmly secure the at least one cradle support strut to the cradle seat, the at least one sliding lock shaft being laterally moveable between (i) a first sliding lock shaft position wherein the second locking moiety is engaged with the first locking moiety so as to firmly secure the at least one cradle support strut to the cradle seat, and (ii) a second sliding lock shaft position wherein the second locking moiety is disengaged from the first locking moiety so that the at least one support strut is capable of being lifted off of the cradle seat;

(d) coupling means for urging the sliding lock shaft to the first sliding lock shaft position and for urging each conduit connection and electrical connection moiety in the second apparatus component towards a corresponding conduit connection or electrical connection moiety in the first apparatus component in such a way that each conduit connection and electrical connection moiety in the second apparatus component is operatively coupled to a corresponding conduit connection or electrical connection moiety in the first apparatus component; and (e) decoupling means for urging the sliding lock shaft to the second sliding lock shaft position and for urging each conduit connection and electrical connection moiety in the second apparatus component away from a corresponding conduit connection or electrical connection moiety in the first apparatus component in such a way that each conduit connection and electrical connection moiety in the second apparatus component is effectively decoupled from all conduit connection and electrical connection moieties in the first apparatus component, whereby the second apparatus component can be physically separated from the first apparatus component.

2. The modular apparatus of claim 1 wherein the at least one conduit connection or electrical connection moieties comprises a plurality of conduit connection or electrical connection moieties.

3. The modular apparatus of claim 1 wherein the coupling means comprises one or more counterweights.

4. The modular apparatus of claim 1 wherein the first locking moiety comprises a beveled shoulder and the second locking moiety comprises a corresponding chamfer disposed at substantially the same angle as the beveled shoulder so that, when the sliding lock shaft is in the first sliding lock shaft position, the beveled shoulder cooperates with the chamfer to firmly secure the at least one cradle support strut to the cradle seat.

5. The modular apparatus of claim 1 wherein the cradle has a plurality of cradle support struts, each having a first locking moiety, and wherein the at least one sliding lock shaft comprises a plurality of sliding lock shafts, each sliding lock shaft having at least one second locking moiety, the sliding lock shafts being sized and dimensioned so that (i) when the sliding lock shafts are in the first sliding lock shaft positions, each of the second locking moieties is engaged with a first locking moiety, and (ii) when the sliding lock shafts are in the second sliding lock shaft position, none of the second locking mechanisms are engaged with a first locking mechanism.

6. The modular apparatus of claim 1 wherein the cradle has four cradle support struts, each having a first locking moiety, and wherein the at least one sliding lock shaft comprises two sliding lock shafts, each sliding lock shaft having a pair of second locking moieties, the sliding lock shaft being sized and dimensioned so that (i) when the sliding lock shafts are in the first sliding lock shaft position, each of the second locking moieties are engaged with a first locking moiety, and (ii) when the sliding lock shafts are in the second sliding lock shaft position, none of the second locking moieties is engaged with a first locking moiety.

7. The modular apparatus of claim 1 wherein the at least one sliding lock shaft is moved between the first sliding lock shaft position and the second sliding lock shaft position by rack and pinion gears.

8. The modular apparatus of claim 7 wherein the coupling means comprises one or more counterweights and wherein the pinion gears are rotated in one direction by lowering the counterweights.

9. A modular apparatus having at least one fluid stream conduit or one electrical circuit, the apparatus comprising:

(a) a first apparatus component attached to a cradle, the cradle having a plurality of cradle support struts, the cradle support struts each comprising a first locking moiety, the first apparatus component also having at least one conduit connection or one electrical connection moiety;

(b) a second apparatus component having at least one conduit connection or electrical connection moiety, each of the at least one conduit connection or electrical connection moieties of the second apparatus component being operatively aligned with one of the at least one conduit connection or electrical connection moieties of the first apparatus component to form one or more corresponding pairs of conduit connection or electrical connection moieties, each corresponding pair of conduit connection or electrical connection moieties being (i) connectable to one another by axial thrusting of one moiety in the corresponding pair of conduit connection or electrical connection moieties towards the other moiety, and (ii) disconnectable by axial withdrawal of one conduit connection or electrical connection moiety in the corresponding pair of conduit connection or electrical connection moieties away from the other moiety in that pair of corresponding pair of conduit connection or electrical connection moieties;

(c) at least two sliding lock shafts attached to the second apparatus component, the at least two sliding lock shafts each having at least one cradle seat for accepting and retaining a cradle support strut, each cradle seat comprising a second locking moiety capable of engaging a first locking moiety to firmly secure a cradle support strut to the cradle seat, each sliding lock shaft being laterally moveable between (i) a first sliding lock shaft position wherein each second locking moiety is engaged with a first locking moiety so as to firmly secure each cradle support strut to a cradle seat, and (ii) a second sliding lock position wherein each second locking moiety is disengaged from a first locking moiety so that the support struts are capable of being lifted off of the cradle seats;

(d) one or more counterweights for urging each sliding lock shaft to the first sliding lock shaft position and for urging each conduit connection and electrical connection moiety in the second apparatus component towards a corresponding moiety in the first apparatus component in such a way that each conduit connection and electrical connection moiety in the second apparatus component is operatively coupled to a corresponding moiety in the first apparatus component, and (e) means for urging each sliding lock shaft to the second sliding lock shaft position and for urging each conduit connection and electrical connection moiety in the second apparatus component away from a corresponding moiety in the first apparatus component in such a way that each conduit connection and electrical connection moiety in the second apparatus component is effectively decoupled from all conduit connection and electrical connection moieties in the first apparatus component, whereby the second apparatus component can be physically separated from the first apparatus component.

10. The modular apparatus of claim 9 wherein the at least one conduit connection or electrical connection moiety comprises a plurality of conduit connection or electrical connection moieties.

11. The modular apparatus of claim 9 wherein the first locking moiety comprises a beveled shoulder and the second locking moiety comprises a chamfer disposed at substantially the same angle as the beveled shoulder so that, when the sliding lock shaft is in the first sliding lock shaft position, the beveled shoulder cooperates with the chamfer to firmly secure the at least one cradle support strut to the cradle seat.

12. The modular apparatus of claim 9 wherein the cradle has four cradle support struts, each having a first locking moiety, and wherein the at least one sliding lock shaft comprises two sliding lock shafts, each sliding lock shaft having a pair of second locking moieties, the sliding lock shaft being sized and dimensioned so that (i) when the sliding lock shafts are in the first sliding lock shaft position, each of the second locking moieties are engaged with a first locking moiety, and (ii) when the sliding lock shafts are in the second sliding lock shaft position, none of the second locking moieties is engaged with a first locking moiety.

13. The modular apparatus of claim 9 wherein the at least two sliding lock shafts are moved between the first sliding lock shaft position and the second sliding lock shaft position by rack and pinion gears and wherein the pinion gears are rotated in one direction by raising or lowering the counterweights.

14. A modular apparatus having at least one fluid stream or one electrical circuit, the apparatus comprising:
(a) a first apparatus component attached to a cradle, the cradle having four cradle support struts, the cradle support struts each comprising a first locking moiety, the first apparatus component also having at least one conduit connection or electrical connection moiety;
(b) a second apparatus component having at least one conduit connection or electrical connection moiety, each of the at least one conduit connection or electrical connection moieties of the second apparatus component being operatively aligned with one of the at least one conduit connection or electrical connection moieties of the first apparatus component to form one or more corresponding pairs of conduit connection or electrical connection moieties, each corresponding pair of conduit connection or electrical connection moieties being (i) connectable to one another by axial thrusting of one moiety in the corresponding pair of conduit connection or electrical connection moieties towards the other moiety, and (ii) disconnectable by axial withdrawal of one moiety in the corresponding pair of conduit connection or electrical connection moieties away from the other moiety in that corresponding pair of conduit connection or electrical connection moieties;
(c) two sliding lock shafts attached to the second apparatus component, the two sliding lock shafts each having a pair of cradle seats each for accepting and retaining a cradle support strut, each cradle seat comprising a second locking moiety capable of engaging a first locking moiety to firmly secure a cradle support strut to the cradle seat, each sliding lock shaft being laterally moveable between (i) a first sliding lock shaft position wherein each second locking moiety is engaged with a first locking moiety so as to firmly secure each cradle support strut to a cradle seat, and (ii) a second sliding shaft lock position wherein each second locking moiety is disengaged from a first locking moiety so that the support struts are capable of being lifted off of the cradle seats;
(d) one or more counterweights for urging each sliding lock shaft to the first sliding lock shaft position and for urging each conduit connection and electrical connection moiety in the second apparatus component towards a corresponding conduit connection or electrical connection moiety in the first apparatus component in such a way that each conduit connection and electrical connection moiety in the second apparatus component is operatively coupled to a conduit connection or electrical connection moiety in the first apparatus component; and
(e) means for urging each sliding lock shaft to the second sliding lock shaft position and for urging each conduit connection and electrical connection moiety in the second apparatus component away from a corresponding conduit connection or electrical connection moiety in the first apparatus component in such a way that each conduit connection and electrical connection moiety in the second apparatus component is effectively decoupled from all conduit connection and electrical connection moieties in the first apparatus component, whereby the second apparatus component can be physically separated from the first apparatus component;
wherein the sliding lock shafts are moved between the first sliding lock shaft position and the second sliding lock shaft position by a gear which is rotated in one direction by lowering the counterweights; and
wherein the first locking moiety comprises a beveled shoulder and the second locking moiety comprises a chamfer disposed at substantially the same angle as the beveled shoulder so that, when the sliding lock shaft is in the first sliding lock shaft position, the beveled shoulder cooperates with the chamfer to firmly secure the at least one cradle support strut to the cradle seat.

15. The modular apparatus of claim 14 wherein the at least one conduit connection or electrical connection moiety comprises a plurality of conduit connection or electrical connection moieties.

* * * * *